United States Patent [19]
Miyauchi et al.

[11] Patent Number: 6,045,801
[45] Date of Patent: Apr. 4, 2000

[54] HAIR GROWERS HAVING ACTIONS OF PROMOTING PROLIFERATION OF HAIR PAPILLA CELLS

[75] Inventors: Yutaka Miyauchi, Takasaki; Shigeo Hasegawa, Saitama-ken, both of Japan

[73] Assignee: Yutaka Miyauchi, Gunma-ken, Japan

[21] Appl. No.: 09/107,448

[22] Filed: Jun. 30, 1998

[51] Int. Cl.$^7$ ....................................................... C12N 9/14
[52] U.S. Cl. .................................... 424/195.1; 424/70.14; 530/370
[58] Field of Search ............................... 424/70.14, 195.1; 530/370

[56] References Cited

FOREIGN PATENT DOCUMENTS

| | | |
|---|---|---|
| 55-31001 | 3/1980 | Japan . |
| 56-166107 | 12/1981 | Japan . |
| 57-6402 | 2/1982 | Japan . |
| 1-20123 | 4/1989 | Japan . |
| 3-227911 | 10/1991 | Japan . |

*Primary Examiner*—Herbert J. Lilling
*Attorney, Agent, or Firm*—Nikaido, Marmelstein Murray & Oram LLP

[57] ABSTRACT

Astragali radix extract, which was used as a starting material, was purified over various kinds of column chromatography (activated carbon, Amberlite IR-120B [H$^+$], cellulose, Sephadex G25 and HPLC) to isolate a peptide as a white powder. This peptide is a water-soluble neutral substance and shows positive reactions to ninhydrin and sodium nitroprusside and negative reactions to anisaldehyde, phenolsulfuric acid and Dragendorff reagent. Amino acids constituting the peptide of the present invention contain aspartic acid and oxylysine in large amounts. The peptide of the present invention were successful in promoting 150% proliferation of rabbit hair papilla cells when applied in a concentration of 1.4 μg/ml.

4 Claims, 1 Drawing Sheet

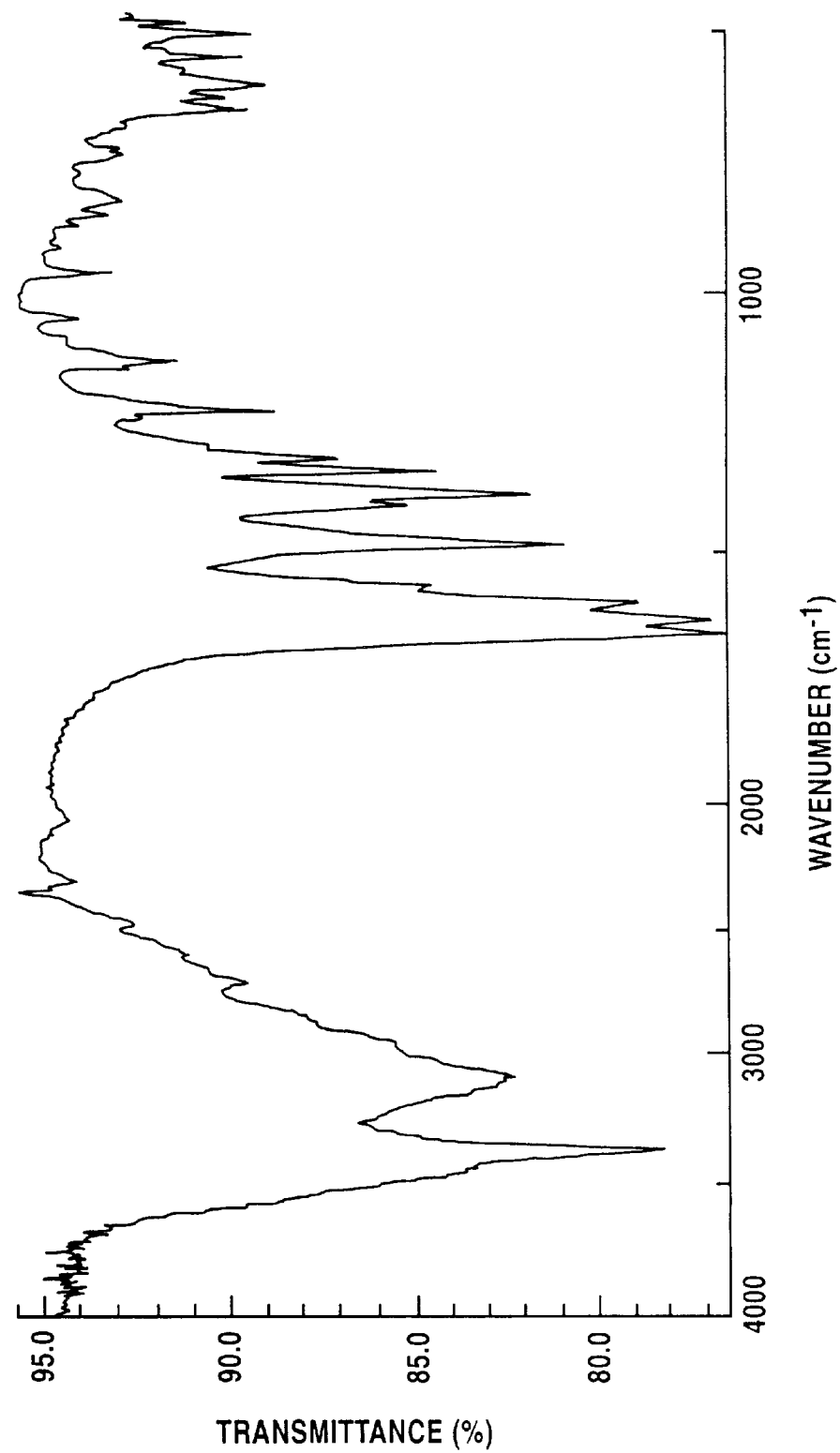

HAIR GROWERS HAVING ACTIONS OF PROMOTING PROLIFERATION OF HAIR PAPILLA CELLS

BACKGROUND OF THE INVENTION

1. Field of the Invention

The present invention relates to hair growers containing specific medical herbal extract or a peptide deriving from the medical herb having actions of promoting proliferation of hair papilla cells, actions of promoting restoration and growth of hair and being effective to prevent loss of hair.

2. Prior Art

While there may be given, as causes of hair loss, factors including reduction in the function of hair follicles under the influence of male hormone, reduction in the metabolic function of hair follicles and hair bulbs, reduction in the physiological function of scalp, local bloodstream disturbance due to strain of scalp, oligotrophy, stress, side effects of drugs, inheritance, etc., the causes of hair loss have not fully been clarified. Accordingly, active ingredients contained in commercially available hair growers act to promote blood circulation in the scalp, to stimulate hair bulbs or to invigorate hair follicles to activate secondarily hair-related cells.

There are demands for hair growers which activate directly hair-related cells based on fundamental studies on the hair growth mechanism and hair loss mechanism. In view of such demands, it is an objective of the present invention to provide hair growers containing a medical herbal extract or a peptide obtained therefrom which act directly upon hair papilla cells taking charge of the hair growth mechanism to promote proliferation of hair-related cells and also hair growers containing the peptide.

SUMMARY OF THE INVENTION

The present inventors searched widely natural products for physiologically active substances having actions of promoting proliferation of hair papilla cells to find that specific medical herbal extracts or a novel peptide obtained therefrom has such actions.

The present invention provides hair growers containing an alcoholic extract of a herb selected from the group consisting of astragali radix, coptidis rhizoma, Anacardium occidentale, zingiberis rhizoma, glycyrrhizae radix, auranti fructus immaturus, notopterygii rhizoma, lycii fructus, cyperi rhizoma, bupleuri radix, zanthoxyli fructus, rehmanniae radix, zhi-gan-cao (grilled licorice), cnidii rhizoma, mori cortex, zizyphi fructus, aurantii nobilis pericarpium, angelicae radix, persicae semen, ginseng radix, gentianae radix, Menispermaceae, senegae radix, Apium and actinidiae fructi galla.

(1) Molecular weight: 2,000 to 4,000 (by gel filtration method);
(2) IR absorption spectrum (KBr): as shown in FIG. 1; absorption bands: 3,356, 3,080, 1,676, 1,647, 1,614, 1,500, 1,425, 1,402, 1,358, 1,336, 1,250, 1,151, 1,072 and 985 $cm^{-1}$; UV absorption spectrum (in water) showed no typical absorption peak up to 200 nm;
(3) Solubility: soluble in water, and sparedly or hardly soluble in ether, benzene and chloroform;
(4) Color-forming reaction: positive to ninhydrin reaction and to sodium nitroprusside reaction, and negative to anisaldehyde reaction, phenolsulfuric acid reaction and Dragendorff reaction;
(5) Distinction of basic, neutral and acidic properties: neutral;
(6) Property: Water-white crystals or a white crystalline powder developing peculiar odor slightly; and
(7) Constituent amino acids: The peptide contains phosphoserine, aspartic acid, serine, glutamic acid, glycine, alanine, valine, cystine, methionine, oxylysine, ornithine, lysine and hystidine in a molar ratio of about 8:9,174:84:4:6:4:4:17:2:13,606:2:1:2, provided that lysine is 1, and it contains oxylysine and aspartic acid in large amounts. The peptide also contains taurine, phosphoethanolamine and urea.

The peptide as an active ingredient in the hair growers of the present invention can be prepared as follows:

The said herbs are subjected to extraction with an alcohol such as methanol and ethanol, and the extract is filtered. The alcohol in the filtrate obtained is distilled off to obtain a dry product. The dry product is dissolved in a purified water to prepare an aqueous solution.

The aqueous solution thus obtained is further subjected to adsorption on an ion-exchange resin and the like and elution with an eluent such as dilute ammonia water, followed by concentration of the eluate under reduced pressure to obtain a crude material. The ion-exchange resin can typically be exemplified by Amberlite IR-120B[$H^+$] as a strong-acidity cation-exchange resin.

The crude material obtained can be purified by known methods employed conventionally for purification of water-soluble substances, for example, by column chromatography employing a carrier such as activated carbon, cellulose, Sephadex G-25, silica gel and gel filtration or by high-performance liquid chromatography employing an ion-exchange carrier.

The thus obtained peptide is dissolved in water or a hydrous alcohol, or various kinds of components, commonly used in hair grooming preparations may, as necessary, added to the herbal extract. The mixture can be employed in the form of hair tonic, shampoo, hair cream or the like. Particularly, a preparation further incorporated with a germicidal component such as an aloe extract is preferred.

Contents of the present invention are not to be limited to the above description, and the objective, advantages, features and uses of the present invention will be understood more clearly by reading the following description with reference to the attached drawing. Further, it should be understood that suitable modifications made without departing from the spirit of the present invention shall all be included within the scope of the present invention.

BRIEF DESCRIPTION OF THE DRAWINGS

FIG. 1 shows an IR absorption spectrum of the peptide according to the present invention.

DETAILED DESCRIPTION OF THE PREFERRED EMBODIMENTS

EXAMPLE 1

To 100 g of Astragali radix was added 1,000 ml of 50 v/v % methanol and was stirred well to obtain an extract. This extract was filtered to remove precipitate, and the filtrate was subjected to distillation under reduced pressure to remove the methanol and to be concentrated to dryness. The crude extract thus obtained was dissolved in 2 lit. of a purified water to prepare an aqueous solution, and the solution was applied to an activated carbon column. The liquid passed through the column was combined with washing fractions, and the resulting mixture was applied to an adsorption column of a strong-acidity cation-exchange resin Amberlite IR-120B [$H^+$]. The active fraction was eluted, concentrated, dried and set up with a 0.5 N ammonia water to give approximately 5 g of crude powder.

The crude powder was subjected to cellulose column chromatography, and after the column was washed with 2 lit. each of butanol:acetic acid:water=20:1:1, 10:1:1 and 5:1:1, the active substance was eluted with 2 lit. of an eluent, butanol:acetic acid:water=3:1:1, to obtain 1.5 g of crude purified product, The crude purified product was subjected to gel filtration (developing solvent:water) using Sephadex G-25 as a carrier to obtain 600 mg of crude purified product. The product was then subjected to cellulose column chromatography, and after the column was washed with 0.5 lit. each of ethanol:water=7.5:1 and =5:1, the active substance was eluted with 1 lit. of an eluent, ethanol:water=3:1 to 1:3, to obtain 100 mg of crude purified product, The product was further subjected to cation-exchange type high-performance liquid chromatography (developing solvent:water) to give 5 mg of hair papilla cell proliferation promotor.

Test Example 1

Effects on hair papilla culture cells of rabbit whiskers

Whisker hair papillae separated from a Japanese white rabbit were inoculated to a surface of a collagen (type IV)-coated dish to carry out culturing, according to-a modification of the method of Katuoka, K., et al.: Arch. Dermatol. Res., 279, 20–25 (1986), in a Dulbecco-modified Eagle medium (DMEM) having 20% fetal bovine serum (FBS) and an antibiotic added thereto to obtain primary culture cells migrated from the whisker hair papillae. These cells were subcultured in a 10% FBS-DMEM to obtain hair papilla culture cells. An assay was carried out in the following manner: The hair papilla culture cells were suspended in a 10% FBS-DMEM, and the resulting suspension was seeded on a 96-well plate and cultured for 6 days with addition of an aqueous solution of the peptide obtained in Example 1 having a predetermined concentration twice in the meantime. Presence or absence of proliferation of the hair papilla culture cells was determined by means of MTT. The results are shown in Table 1.

TABLE 1

| Concentration of hair papilla cell proliferation promotor ($\mu$g/ml) | Proliferation promoting activity (%) |
|---|---|
| 15.6 | 186.5 ± 18.1 |
| 3.9 | 173.7 ± 24.8 |
| 1.0 | 136.2 ± 9.2 |
| 0.25 | 107.1 ± 20.7 |

It can be understood from these results that the peptide of the present invention is effective in a low concentration of 1.4 $\mu$g/ml to promote 150% proliferation of the hair papilla culture cells.

What is claimed is:

1. A peptide derived from herbs, which has the following physicochemical properties:

(1) Molecular weight: 2,000 to 4,000 (by gel filtration method);

(2) IR absorption spectrum (KBr): as shown in FIG. 1;

(3) Solubility: soluble in water, and sparedly or hardly soluble in ether, benzene and chloroform;

(4) Color-forming reaction: positive to ninhydrin reaction and to sodium nitroprusside reaction; and negative to anisaldehyde reaction, phenolsulfuric acid reaction and Dragendorff reaction;

(5) Distinction of basic, neutral and acidic properties: neutral;

(6) Property: water-white crystals or white crystalline powder developing specific odor slightly; and (7) Constituent amino acids: aspartic acid and oxylysine.

2. The peptide according to claim 1 containing phosphoserine, aspartic acid, serine, glutamic acid, glycine, alanine, valine, cystine, methionine, oxylysine, ornithine, lysine and hystidine.

3. The peptide according to claim 1 further comprising an aloe extract.

4. The peptide according to claim 2 further comprising an aloe extract.

* * * * *